(12) United States Patent
Bonutti et al.

(10) Patent No.: US 10,219,933 B2
(45) Date of Patent: *Mar. 5, 2019

(54) PRONATION/SUPINATION ORTHOSIS AND METHOD

(71) Applicant: BONUTTI RESEARCH, INC., Effingham, IL (US)

(72) Inventors: Peter M. Bonutti, Manalapan, FL (US); Boris P. Bonutti, Effingham, IL (US); Kevin R. Ruholl, Teutopolis, IL (US); Glen A. Phillips, Effingham, IL (US)

(73) Assignee: Bonutti Research, Inc., Effingham, IL (US)

( * ) Notice: Subject to any disclaimer, the term of this patent is extended or adjusted under 35 U.S.C. 154(b) by 489 days.

This patent is subject to a terminal disclaimer.

(21) Appl. No.: 14/991,453

(22) Filed: Jan. 8, 2016

(65) Prior Publication Data
US 2016/0120682 A1    May 5, 2016

Related U.S. Application Data

(63) Continuation of application No. 14/202,633, filed on Mar. 10, 2014, now Pat. No. 9,259,344, which is a
(Continued)

(51) Int. Cl.
*A61F 5/01*    (2006.01)

(52) U.S. Cl.
CPC ...... *A61F 5/013* (2013.01); *A61F 2005/0165* (2013.01)

(58) Field of Classification Search
CPC .. A61H 1/0274; A61H 1/0237; A61H 1/0262; A61H 2201/5058; A61H 2201/165; A61H 1/0277; A61H 2201/1215; A61H 2201/1638; A61H 1/0285; A61H 2201/5064; A61H 2201/5082; A61H 23/02; A61H 1/02; A61F 2005/0165; A61F 5/013; A61F 5/373; A61F 5/3723; A61F 5/3715; A61F 5/37; A61F 5/0102;
(Continued)

(56) References Cited

U.S. PATENT DOCUMENTS

| 4,191,373 | A |   | 3/1980 | Lancellotti |
| 5,213,094 | A | * | 5/1993 | Bonutti ............ A61F 5/0123 601/33 |

(Continued)

FOREIGN PATENT DOCUMENTS

| CN | 2516187 Y | 10/2002 |
| CN | 1480119 A | 3/2004 |
| CN | 1988862 A | 6/2007 |

*Primary Examiner* — Tarla R Patel
(74) *Attorney, Agent, or Firm* — Stinson Leonard Street LLP

(57) ABSTRACT

An orthosis for supination and/or pronation of a forearm of a wearer, the orthosis including a base, an upper arm support coupled to the base and configured to secure an upper arm of the wearer, a rotation assembly coupled to the base and including an output member rotatable relative to the base within a rotation plane, and a forearm support member coupled to the output member of the rotation assembly and configured to releasably engage a wrist and the forearm of the wearer.

17 Claims, 4 Drawing Sheets

Related U.S. Application Data continuation of application No. 13/232,337, filed on Sep. 14, 2011, now Pat. No. 8,708,939.

(58) Field of Classification Search
CPC ...... A61F 2002/543; A61F 2/58; A61F 2/582; A61F 2/38; A61F 2/3804; A61F 2007/0032; A61F 13/101
USPC .............................................. 602/16, 20–28
See application file for complete search history.

(56) References Cited

U.S. PATENT DOCUMENTS

| | | | |
|---|---|---|---|
| 5,219,323 A | 6/1993 | Singer et al. | |
| 5,759,165 A | 6/1998 | Malewicz | |
| 5,848,979 A | 12/1998 | Bonutti et al. | |
| 5,951,499 A | 9/1999 | Saringer et al. | |
| 6,179,799 B1 | 1/2001 | Doran | |
| 6,740,051 B2 | 5/2004 | Hepburn et al. | |
| 6,866,646 B2 * | 3/2005 | Hopkins | A61F 5/013 602/16 |
| 7,101,347 B2 | 9/2006 | Culhane et al. | |
| 7,618,381 B2 | 11/2009 | Krebs et al. | |
| 8,708,939 B2 * | 4/2014 | Bonutti | A61F 5/013 602/16 |
| 9,259,344 B2 | 2/2016 | Bonutti et al. | |
| 2003/0105416 A1 | 6/2003 | Hepburn et al. | |
| 2009/0030353 A1 | 1/2009 | Bonutti et al. | |
| 2009/0054820 A1 | 2/2009 | Weltner et al. | |
| 2009/0326422 A1 | 12/2009 | Hoffman et al. | |

\* cited by examiner

PRONATION/SUPINATION ORTHOSIS AND METHOD

CROSS REFERENCE TO RELATED APPLICATIONS

This application is a continuation application of U.S. patent application Ser. No. 14/202,633, filed Mar. 10, 2014, which is a continuation application of U.S. patent application Ser. No. 13/232,337, filed Sep. 14, 2011, each of which is incorporated herein by reference in its entirety.

BACKGROUND

The field of the disclosure relates generally to a hand and forearm orthosis. When a joint is injured either by trauma or by surgery, scar tissue can form, often resulting in contractures. Such conditions can limit the range of motion of the joint. It is often possible to treat this condition by use of a range-of-motion (ROM) orthosis. ROM orthoses are devices commonly used during physical rehabilitative therapy to increase the range-of-motion over which the wearer can move the joint.

BRIEF DESCRIPTION

An orthosis for supination and/or pronation of a forearm of a wearer is provided. The orthosis including a base, an upper arm support coupled to the base and configured to secure an upper arm of the wearer, a rotation assembly coupled to the base and including an output member rotatable relative to the base within a rotation plane, and a forearm support member coupled to the output member of the rotation assembly and configured to releasably engage a wrist and the forearm of the wearer.

An orthosis for supination and/or pronation of a forearm of a wearer is provided. The orthosis including a base, an upper arm support coupled to the base and configured to engage an upper arm of the wearer, a rotation assembly coupled to the base and including an output member rotatable relative to the base within a rotation plane, and a forearm support member coupled to the output member of the rotation assembly, such that the forearm support member is configured to substantially align a styloid process of the wearer with a rotational plane of the rotation assembly.

A method of using an orthosis for supination and/or pronation of a forearm of a wearer is provided. The method including coupling an upper arm of the wearer to the orthosis, and coupling a wrist and the forearm of the wearer to a forearm support member of the orthosis such that a styloid process of the wearer is substantially aligned with a rotation plane of a rotation assembly.

A method of using an orthosis for supination and/or pronation of a forearm of a wearer is provided. The method including coupling an upper arm of the wearer to the orthosis, coupling a wrist and the forearm of the wearer to a forearm support member of the orthosis such that the forearm support member extends to a location proximal the wrist of the wearer, and initiating a rotation assembly to rotate the wrist of the wearer.

DETAILED DESCRIPTION

This disclosure relates generally to an orthosis for providing supination and pronation rotation of a forearm of a wearer. The orthosis provides rotation such that an upper arm portion of the wearer is secured in a position relative to the rotation of a forearm of the wearer.

Figure 1:
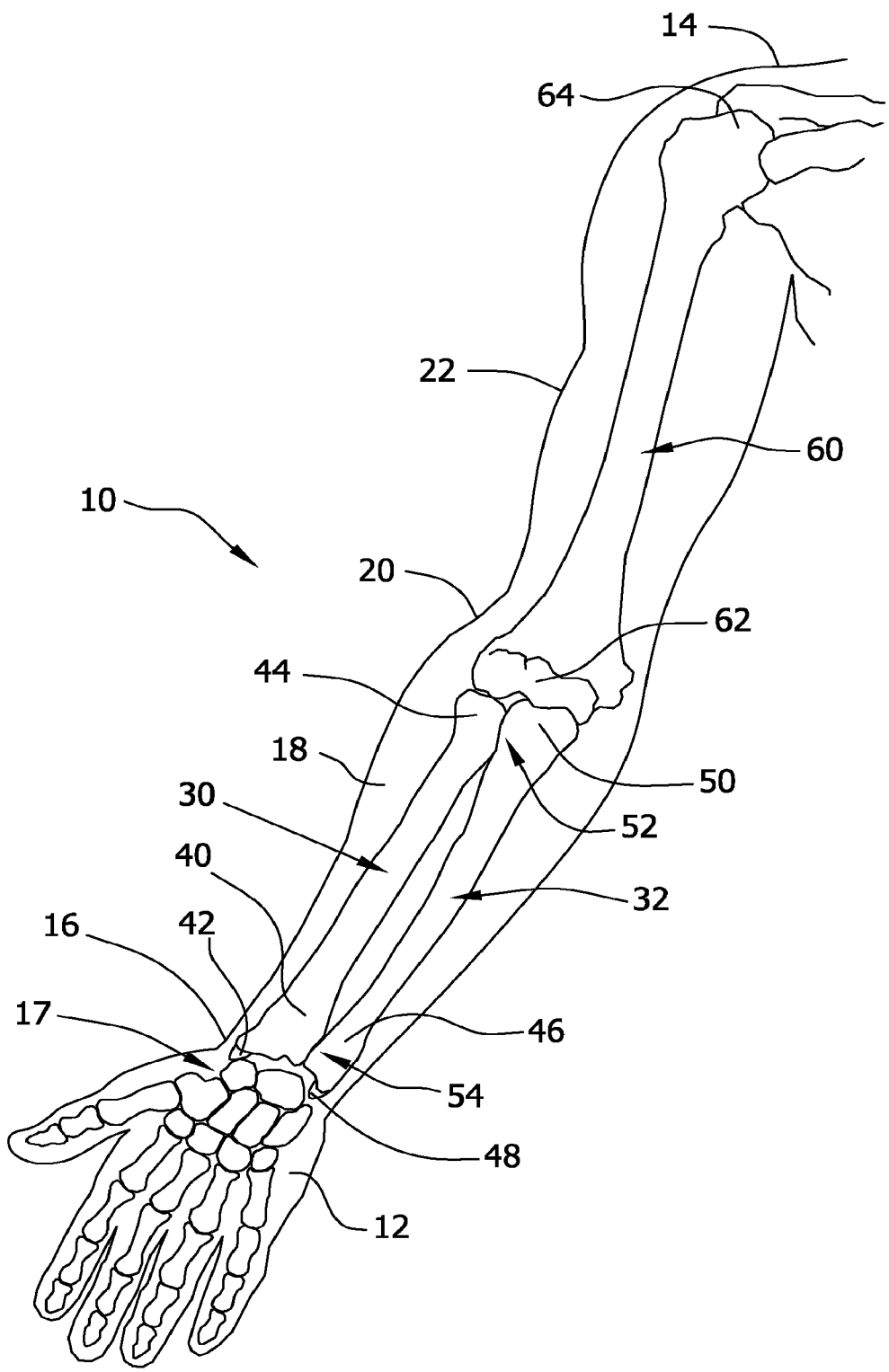
FIG. 1 is an illustration of a right anterior arm of a wearer.

FIG. 1 is an illustration of an arm of a wearer for use with an orthosis. Although the orthosis could be utilized with either a right or left arm of the wearer, a right arm 10 of the wearer is illustrated in FIG. 1. Arm 10 of the wearer extends between a hand 12 and a shoulder 14 of the wearer. Right arm 10 of the wearer includes a wrist 16, a lower portion or forearm 18, an elbow 20, and an upper portion 22. Wrist 16 includes carpals 17 is the region where hand 12 is joined with lower portion 18 of arm 10 of the wearer. Elbow 20 is the region where lower portion 18 of arm 10 and upper portion 22 of arm 10 are joined.

Lower portion 18 of arm 10 includes a radius bone 30 and an ulna bone 32. Radius 30 has a distal end portion 40 at the end of which a radius styloid process 42 is formed. Radius 30 has a proximal end portion 44 or head of radius 30 at elbow 20. Similarly, ulna 32 has a distal end portion 46 at the end of which an ulna styloid process 48 is formed. Ulna 32 has a proximal end portion or olecranon 50 at elbow 20. Lower portion 18 of arm 10 also includes a proximal radioulnar joint 52 and a distal radioulnar joint 54. The location of radius styloid process 42 and ulna styloid process 48 is substantially at the wrist joint or the location of wrist 16 at which flexion, extension, adduction, abduction, and circumduction occur with hand 12.

Upper portion 22 of arm 10 extends between shoulder 14 and elbow 20. Upper portion 22 of arm 10 includes a humerus bone 60. Humerus 60 has a distal end portion or trochlea and capitulum 62, which cooperates with proximal end portions 44 and 50 of radius 30 and ulna 32 respectively. Additionally, humerus 60 has a proximal end portion 64, which cooperates with shoulder 14.

Pronation of forearm 18 occurs when hand 12 is turned so that the palmar or anterior side of hand 12 and wrist 16 faces downward and the opposite or posterior side of hand 12 and wrist 16 face upward. Supination of forearm 18 occurs when hand 12 is turned so that the palmar or anterior side of hand 12 and wrist 16 faces upward and the opposite or posterior side of hand 12 and wrist 16 face downward. During pronation of forearm 18, radius 30 crosses ulna 32 by revolving about proximal and distal radioulnar joints 52 and 54. The orthosis couples to wrist 16, at least a portion of forearm 18, and upper portion 22 of arm 10 of the wearer to isolate movement to radius 30 and ulna 32 during pronation and/or supination of hand 12.

Figure 2:
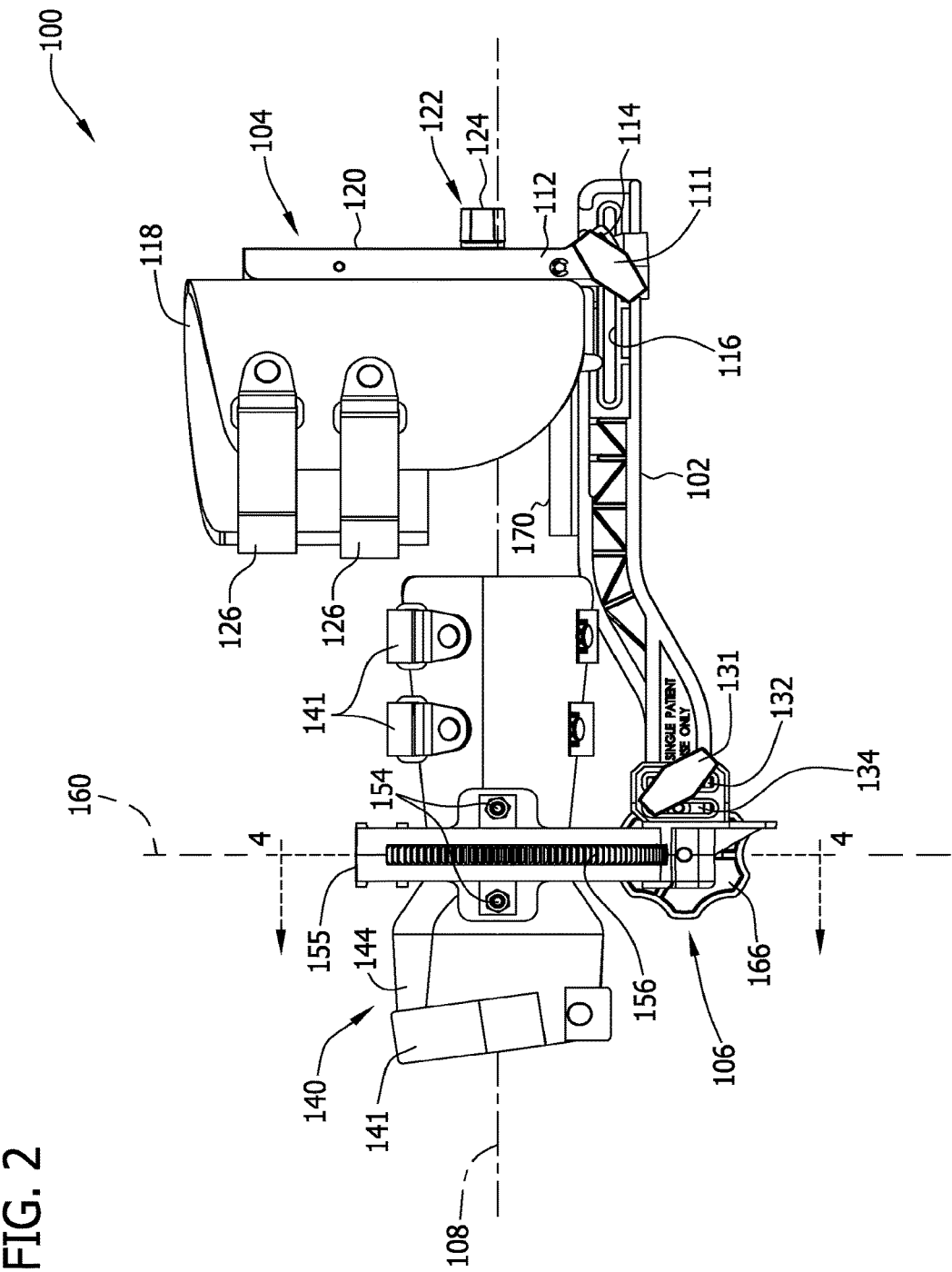
FIG. 2 is side perspective view of an exemplary orthosis for providing supination and pronation rotation.
Figure 3:
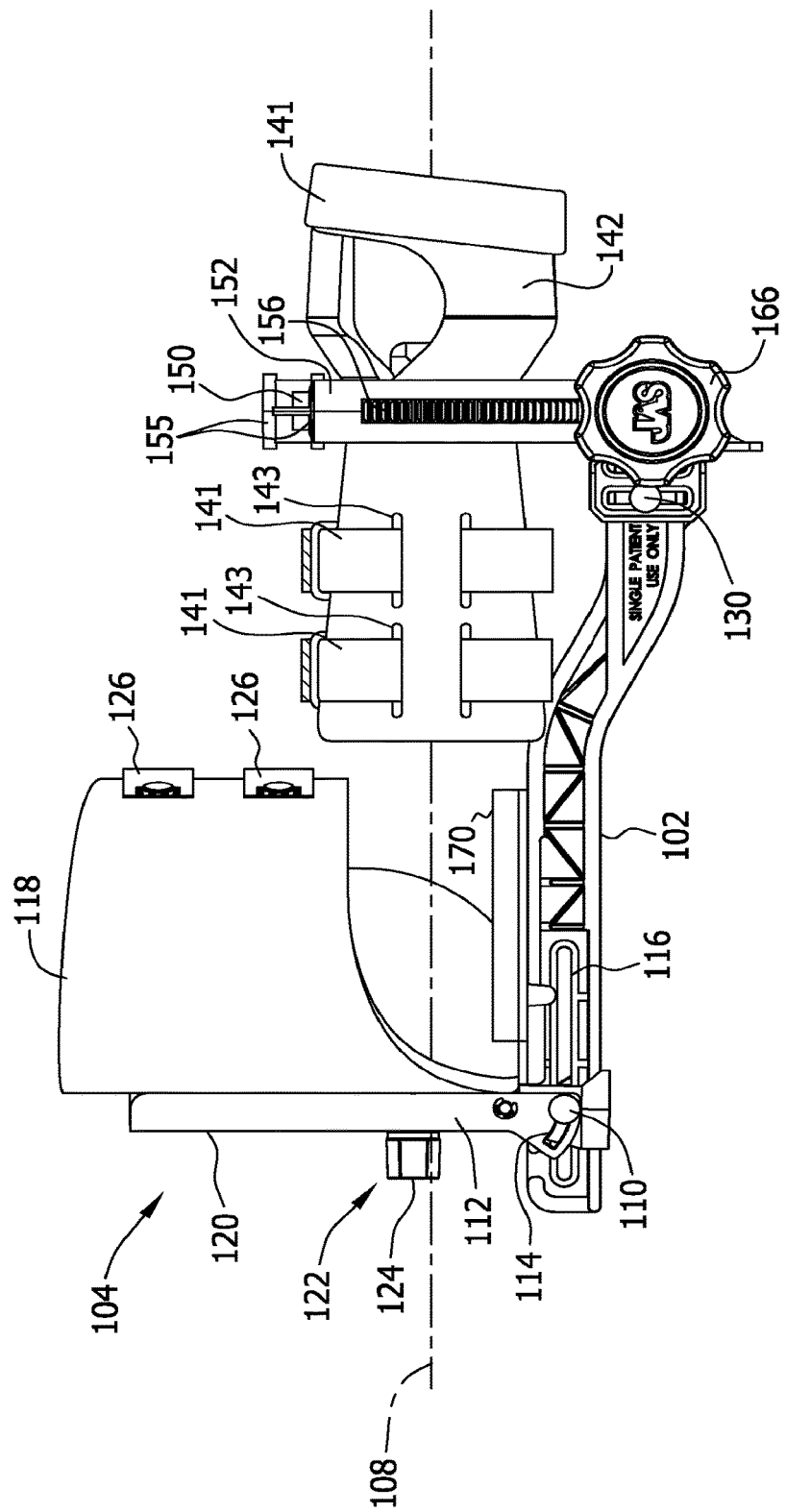
FIG. 3 is an alternative side perspective view of the orthosis of FIG. 2.

FIGS. 2 and 3 are side perspective views of an exemplary orthosis for providing supination and pronation rotation of an arm 10 of a wearer shown in FIG. 1. In the exemplary embodiment, an orthosis 100 includes a base 102 that may be releasably coupled to an upper arm support 104 and rotation assembly 106 having a central axis 108 extending longitudinally through the device with respect to base 102. Base 102 may be releasably coupled to an upper arm support 104 via a retention device 110 and in the exemplary embodiment, base 102 may be formed from a rigid plastic material but may be formed from any suitable material. Retention device 110 may be a locking device in the exemplary embodiment and may be in the form of a bolt and knob 111, which facilitates selective locking and unlocking of upper arm support 104 to base 102. Upper arm support 104 includes an arm member 112 positionable over base 102 such that a slot 114 may be formed within arm member 112 to enable upper arm support 104 to couple to base 102. Arm member 112 may be formed from a rigid plastic material but may be formed from any suitable material. In one embodiment, slot 114 may be substantially arcuate to allow upper arm support 104 to provide adjustment of an angle formed between upper arm support 104 and base 102. Base 102 includes a retention slot 116 substantially aligned with a longitudinal axis of base 102 and substantially parallel with central axis 108 such that upper arm support 104 may be slidably coupled to base 102, to accommodate wearers of orthosis 100 having forearms 18 of various lengths.

Upper arm support 104 also includes an upper arm cuff 118 configured to secure upper arm 22 to orthosis 100. Upper arm support 104 substantially secures upper arm portion 22 of the wearer in a fixed position relative to hand 12 of the wearer during rotation. Upper arm cuff 118 may be releasably coupled to arm member 112, through cuff slot 120, via cuff retainer 122. In one embodiment, cuff retainer 122 includes a bolt (not shown) extending through upper arm cuff 118 and cuff slot 120 that may be tightened and secured by cuff knob 124. Alternatively, upper arm cuff 118 may be coupled to arm member 112 by a any suitable retention means. In the exemplary embodiment, upper arm cuff 118 may be fabricated from a resilient material, such as plastic, and includes upper arm straps 126 coupled to upper arm cuff 118 that may be configured to allow upper arm cuff 118 to releasably secure an upper arm of the wearer within upper arm support 104. In an alternative embodiment, upper arm cuff 118 may be fabricated from a relatively rigid material that substantially prevents movement of upper arm cuff 118. Upper arm straps 126 include a releasable fastening component, such as hook and loop components, to adjustably tighten strap 126 and releasably secure upper arm 22 to upper arm support 104.

Similar to upper arm support 104, rotation assembly 106 may be slidably coupled to base 102 such that rotation assembly 106 may be positioned over base 102. Rotation assembly 106 may be formed from a rigid plastic material or from another suitable material. In the exemplary embodiment, rotation assembly 106 may be coupled to base 102 via a retention device 130. Retention device 130 extends through a slot 132 formed in rotation assembly 106 and a hole 134 formed within base 102. In the exemplary embodiment, retention device may be a locking device, which may be in the form of a bolt and knob 131 that facilitates selective locking and unlocking of rotation assembly 106 to base 102. Slot 132 may be oriented perpendicular to the longitudinal axis of base 102 to provide vertical adjustment of a hand 12 and/or a wrist 16 with respect to base 102.

Rotation assembly 106 may be configured to rotate forearm 18 about axis 108, which extends substantially within a central or mediolateral axis of forearm 18 of the wearer, when positioned within orthosis 100. In the exemplary embodiment, rotation assembly 106 may be coupled to a forearm support member 140, which includes an anterior forearm support member 142 and a posterior forearm support member 144. Forearm support member 140 may be configured to extend proximal radius styloid process 42, ulna styloid process 48, and the wrist joint of the wearer to provide relative stability and to ensure forearm 18 and wrist 16 may be substantially maintained within axis 108. Forearm support member 140 may be configured to substantially prevent a torsional load from being applied to carpals 17 of wrist 16 and to substantially prevent wrist 16 from extending and/or flexing during rotation of forearm 18 within orthosis 100. Substantially preventing wrist 16 from extending and/or flexing during rotation of forearm 18 facilitates a reduction of a higher load to be placed on wrist 16 and hand 12 than forearm 18.

In the exemplary embodiment, anterior forearm support member 142 and posterior forearm support member 144 may be coupled together via lower arm straps 141, which loop through slots 143 formed within anterior forearm support member 142, such that forearm support member may be configured to secure forearm 18 within forearm support member 140 during rotation of forearm 18. In the exemplary embodiment, lower arm straps 141 may be coupled to forearm support member 140 proximal radius styloid process 42, ulna styloid process 48, and the wrist joint. Coupling forearm support member 140 proximal radius styloid process 42, ulna styloid process 48, and the wrist joint facilitates substantially preventing wrist 16 from extending and/or flexing during rotation of hand 12.

In one embodiment, lower arm straps 141 include fastening components, such as hook and loop components, such that straps 141 may be adjustable and may be tightened over hand 12 and forearm 18. In the exemplary embodiment, forearm support member 140 may be formed from plastic or other material and includes a cushioning material lining the inner walls of each of anterior forearm support member 142 and posterior forearm support member 144 to provide comfort to the wearer.

Rotation assembly 106 may be coupled to forearm support member 140 by coupling forearm support member 140 to an inner wall 150 formed within a rotation gear 152. In the exemplary embodiment, rotation gear 152 has a substantially arcuate cross-sectional shape to provide rotation to forearm 18. In the exemplary embodiment, forearm support member 140 may be coupled to inner wall 150 with a screw and nut securing system, however, any coupling means can be used to couple forearm support member 140 to inner wall 150. Alternatively, forearm support member 140 may be integrally formed on rotation gear 152.

Rotation gear 152 includes an arcuate array 156 of gear teeth having a configuration of a portion of a circle. Forearm support member 140 extends upward between opposite ends 155 of arcuate array 156 of gear teeth and through a portion of an opening 158 formed in rotation gear 152. Arcuate array 156 of gear teeth defines a rotational plane 160, which may be perpendicular and/or orthogonal to axis 108. Forearm support member 140 may be coupled to rotation assembly 106 such that, when in use, the wearer's radius styloid process 42 and/or ulna styloid process 48 lie within rotational plane 160. Aligning radius styloid process 42 and/or ulna styloid process 48 with rotational plane 160 facilitates substantially preventing wrist 16 from extending and/or flexing during rotation of forearm 18.

Figure 4:
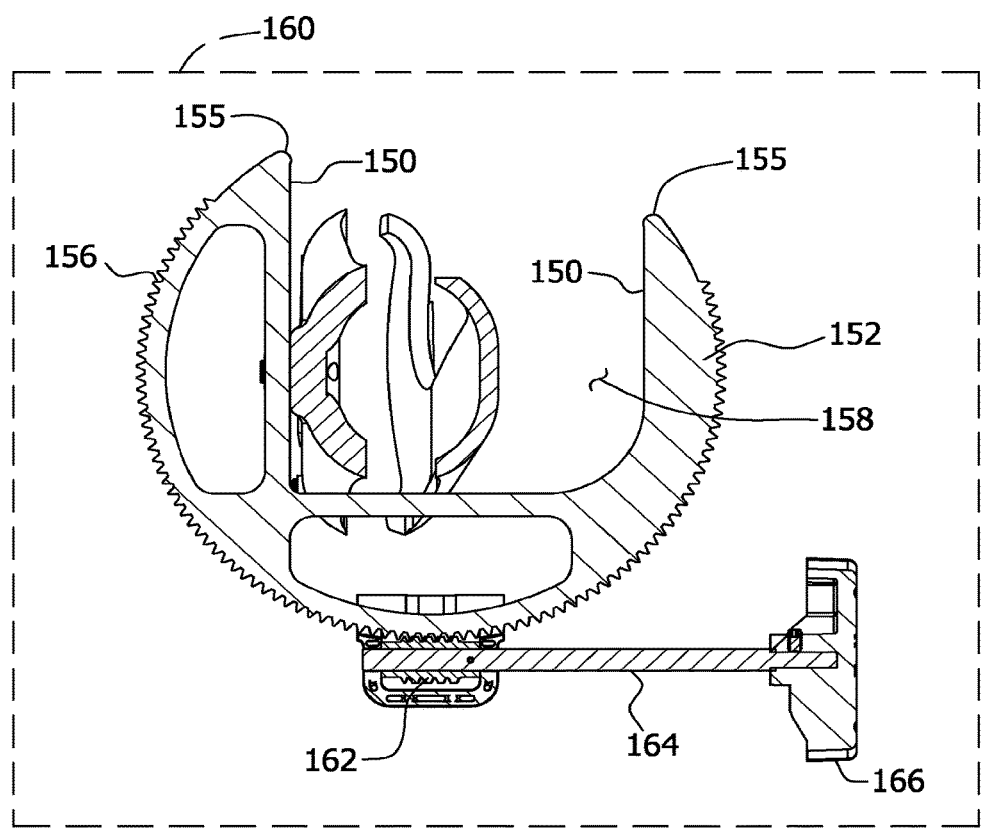
FIG. 4 is a fragmentary sectional view of the orthosis of FIG. 2.

Rotation gear 152 may be coupled to a drive gear 162 (shown in FIG. 4) that may be fixedly coupled with a drive shaft 164 and drive knob 166, such that drive gear 162 may be engaged with arcuate array 156 of teeth on rotation gear 152. In the exemplary embodiment, drive gear 162 may be a worm gear. In an alternative embodiment, drive gear 162 may be a motor. Alternatively, drive gear 162 may be any gear that affects rotation of forearm 18 of the wearer. Upon rotation of drive knob 166, drive gear 162 may be rotated to affect pronation and/or supination of forearm 18.

During operation, in the exemplary embodiment, viscoelastic body tissue connecting proximal end portions 44 and 50 of radius 30 and ulna 32 with humerus 60 in arm 10 of the wearer may require stretching to enable forearm 18 of the wearer to move through a desired range of motion in supination and/or pronation. When the viscoelastic body tissue connected with proximal end portions 44 and 50 of radius 30 and ulna 32 is to be stretched, upper portion 22 of arm 10 of the wearer is positioned in upper arm cuff 118 of orthosis 100. Straps 126 may be tightened around upper portion 22 of arm 10 to position arm member 112 relative to upper portion 22 of wearer's arm 10.

Hand 12 may be positioned in forearm support member 140 by moving hand 12 through opening 158 in forearm support member 140. Straps 141 may be then tightened and secured proximal the wrist joint to press the sidewalls of forearm support member 140 against the palmar and back sides of hand 12, wrist 16, and forearm 18, such that at least one of the radius styloid process 42 and ulna styloid process 48 may be substantially aligned with rotational plane 160. Once hand 12, wrist 16, and forearm 18 may be positioned within forearm support member 140, flexion and/or extension of wrist 16 may be substantially prevented.

Until rotation assembly 106 is actuated or initiated, lower portion 18 and upper portion 22 of wearer's arm 10 may be held against movement relative to each other. Thus, lower portion 18 of arm 10 may be held against movement relative to base 102 by forearm support member 140. Upper portion 22 of arm 10 may be held against movement relative to arm member 112 by upper arm cuff 118.

To affect pronation of forearm 18, knob 166 of rotation assembly 106 may be rotated in a counterclockwise direction. Counterclockwise rotation of knob 166 causes drive gear 162 to rotate rotation gear 152 about axis 108. As rotation occurs, anterior forearm support member 142 and a posterior forearm support member 144 of forearm support member 140 secure hand 12, wrist 16, and forearm 18 to substantially prevent a torsional load from being placed on carpals 17 and to substantially prevent flexion and/or extension of the wrist joint and allow distal end portions 40 and 46 of radius 30 and ulna 32 to rotate with forearm support member 140 about axis 108.

As forearm support member 140 is rotated about axis 108, proximal end portions 44 and 50 of radius 30 and ulna 32 move relative to distal end portion 102 of humerus 60. Proximal end portion 50 of ulna 32 articulates with distal end portion 102 of humerus 60. The rotational motion imparted by forearm support member 140 to distal end portions 40 and 46 of radius 30 and ulna 32 may be isolated to the region between elbow 20 and wrist 16 in arm 10 of the wearer. As drive gear 162 is rotated, rotation gear 152 and forearm support member 140 may be rotated together in a clockwise direction about axis 108 and the extent of pronation of forearm 18 may be increased.

Reversing the direction of rotation of knob 166 rotates drive gear 162 and rotation gear 152 to move forearm support member 140 such that the extent of pronation of forearm 18 may be decreased. Rotation assembly 106 may be operated to increase the extent of supination of forearm 18 by rotating knob 166 in a clockwise direction. As forearm support member 140 and rotation gear 152 may be rotated in a counterclockwise direction, the extent of supination of forearm 18 may be increased. As forearm 18 is rotated, anterior forearm support member 142 and posterior forearm support member 144 of forearm support member 140 secure hand 12, wrist 16, and forearm 18 to substantially prevent a torsional load from being placed on carpals 17 and to substantially prevent flexion and/or extension of the wrist joint. Rotating forearm 18, anterior forearm support member 142, and posterior forearm support member 144 allows distal end portions 40 and 46 of radius 30 and ulna 32 to rotate with forearm support member 140 about axis 108 and results in radius 30 and ulna 32 bones being moved relative to humerus 60 at elbow 20.

This written description uses examples to disclose embodiments of the invention, including the best mode, and also to enable any person skilled in the art to practice embodiments of the invention, including making and using any devices or systems and performing any incorporated methods. The patentable scope of this disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An orthosis for supination and/or pronation of a forearm of a wearer, the orthosis comprising:
    a base defining a longitudinal axis;
    an upper arm cuff coupled to the base and configured to be secured to an upper arm of the wearer;
    a rotation assembly coupled to the base and comprising an output member rotatable relative to the base in a rotational plane that is perpendicular to the longitudinal axis of the base;
    a forearm cuff operatively coupled to the output member of the rotation assembly and configured to be secured to the forearm and associated hand and wrist of the wearer, wherein the forearm cuff is sized and shaped to extend from the hand to a location proximal of an associated radius styloid process and ulna styloid process when secured to the wearer; and
    first and second straps coupled to the forearm cuff for use in securing the forearm cuff to the wearer, wherein the first and second straps are coupled to the forearm cuff at spaced apart locations that are proximal of the associated radius styloid process and ulna styloid process when the cuff is secured to the wearer.

2. An orthosis in accordance with claim 1, wherein the forearm cuff is coupled to the rotation assembly such that an ulna styloid process of the wearer is substantially alignable with the rotational plane of the rotation assembly.

3. An orthosis in accordance with claim 2, wherein the gear is operatively connected to the output member such that rotation of the gear rotates the output member.

4. An orthosis in accordance with claim 3, wherein the rotation assembly further comprises a knob operatively connected to the gear and configured to be selectively actuated by the wearer such that rotation of the knob rotates the output member.

5. An orthosis in accordance with claim 1, wherein the forearm cuff is coupled to the rotation assembly such that a radius styloid process of the wearer is substantially alignable with the rotational plane of the rotation assembly.

6. An orthosis in accordance with claim 1, wherein the forearm cuff is configured to substantially prevent a higher load to be placed on the wrist and the hand than the forearm of the wearer.

7. An orthosis in accordance with claim 1, wherein the upper arm cuff is movable relative to the base to adjust an angle between the upper arm cuff and the base.

8. An orthosis in accordance with claim 1, wherein the upper arm cuff is movable relative to the base along the longitudinal axis of the base.

9. An orthosis in accordance with claim 1, wherein the rotation assembly comprises a gear.

10. An orthosis in accordance with claim 1, wherein the forearm cuff is spaced apart from the base by a distance.

11. Au orthosis in accordance with claim 10, wherein the forearm cuff is movable relative to the base to adjust the distance between the forearm cuff and the base.

12. An orthosis in accordance with claim 11, wherein the forearm cuff is movable in a direction that is substantially perpendicular to the longitudinal axis of the base to adjust a heigthwise distance between the forearm cuff and the base.

13. An orthosis in accordance with claim 12, wherein the rotation assembly is movable in the direction that is substantially perpendicular to the longitudinal axis of the base to adjust the heigthwise distance between the forearm cuff and the base.

14. An orthosis in accordance with claim 1, wherein the forearm cuff comprises an anterior forearm support member and a posterior forearm support member releasably coupled together with the first and second forearm straps.

15. An orthosis in accordance with claim 1, wherein the output member is rotatable in both a clockwise and counterclockwise directions.

16. An orthosis in accordance with claim 1, wherein the output member surrounds at least a majority of the forearm cuff.

17. An orthosis in accordance with claim 16, wherein the forearm cuff is disposed in an opening defined by the output member.

\* \* \* \* \*